(12) United States Patent
Nerenberg et al.

(10) Patent No.: US 7,655,635 B2
(45) Date of Patent: *Feb. 2, 2010

(54) SUPPRESSION OF NUCLEAR FACTOR-κB DEPENDENT PROCESSES USING OLIGONUCLEOTIDES

(75) Inventors: Michael I. Nerenberg, San Diego, CA (US); Isao Kitajima, San Diego, CA (US)

(73) Assignee: The Scripps Research Institute, La Jolla, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/115,373

(22) Filed: May 5, 2008

(65) Prior Publication Data

US 2008/0274995 A1    Nov. 6, 2008

Related U.S. Application Data

(63) Continuation of application No. 11/888,342, filed on Jul. 30, 2007, which is a continuation of application No. 10/328,861, filed on Dec. 24, 2002, now Pat. No. 7,268,121, which is a continuation of application No. 08/110,161, filed on Aug. 20, 1993, now Pat. No. 6,498,147, which is a continuation-in-part of application No. 07/887,331, filed on May 22, 1992, now abandoned.

(51) Int. Cl.
*C07H 21/02* (2006.01)
*C07H 21/04* (2006.01)
*A61K 31/70* (2006.01)
*C12Q 1/68* (2006.01)
*C12N 5/00* (2006.01)

(52) U.S. Cl. ............... 514/44; 536/23.1; 536/24.1; 536/24.5; 435/6; 435/375; 435/377

(58) Field of Classification Search ............... None
See application file for complete search history.

(56) References Cited

U.S. PATENT DOCUMENTS 6,069,008 A     5/2000  Bennett et al. ........... 435/375
6,207,646 B1    3/2001  Krieg et al.
6,239,116 B1    5/2001  Krieg et al.
6,653,292 B1    11/2003 Krieg et al.

OTHER PUBLICATIONS

Jen et al., Stem Cells, vol. 18:307-319, 2000.*
Agrawal S., TIBTECH vol. 14:376-387, Oct. 1996.*
Branch A., TIBS vol. 23:45-50, Feb. 1998.*
Baeuerle P.A., "The Inducible Transcription Activator NF-PB: Regulation by Distinct Protein Subunits," *Biochimica et Biophysica Acta*, 1072:63-80 (1991).
Branch A.D., "A good antisense molecule is hard to find", *Trends Biochem. Sci.*, 23(2):45-50 (1998).
Fakler et al., "Short antisense oligonucleotide-mediated inhibition is strongly dependent on oligo length and concentration but almost independent of location of the target sequence", *J. Biol. Chem.*, 269:16187-16194 (1994).
Ghosh et al., "Cloning of the p50 DNA Binding Subunit of NF-PB: Homology to *rel* and *dorsal*," *Cell*, 62:1019-1029 (1990).
Gibbs W.W., "State of shock. Sepsis can be fatal to firms as well as to patients" *Scientific American*, 271(4):133-134 (1994).
Kitajima et al, "Human T-cell Leukemia Virus Type I Tax Transformation is Associated with Increased Uptake of Oligodeoxynucleotides in Vitro and in Vivo*," *J. Biol. Chem.*, 267:25881-25888 (1992).
Libermann et al., "Activation of Interleukin-6 Gene Expression through the NF-PB Transcription Factor," *Molecular Cellular Biology*, 10:2327-2334 (1990).
Nolan et al., "DNA binding and I kappa B inhibition of the cloned p65 subunit of NF-kappa B, a rel-related polypeptide," *Cell*, 64:961-969 (1991).
Ruben et al., "Isolation of a *rel*-Related Human cDNA That Potentially Encodes the 65-kD Subunit of NF-PB," *Science*, 251:1490-1493 (1991).
Staal et al, "Intracellular Thiols Regulate Activation of Nuclear Factor PB and Transcription of Human Immunodeficiency Virus," *Proc. Natl. Acad. Sci.* USA, 87:9943-9947 (1990).
Uhlmann et al., "Antisense Oligonucleotides: A New Therapeutic Principle," *Chemical Reviews*, 90(4):544-584 (1990).

* cited by examiner

*Primary Examiner*—Sean R McGarry
(74) *Attorney, Agent, or Firm*—DLA Piper LLP (US)

(57) ABSTRACT

Antisense oligonucleotides which hybridize with nuclear factor-κB (NF-κB) mRNA and methods of using these oligonucleotides.

11 Claims, 6 Drawing Sheets

No oligo. Sense Antisense

LTR-CAT
% conversion  6.5      6.4      0.3

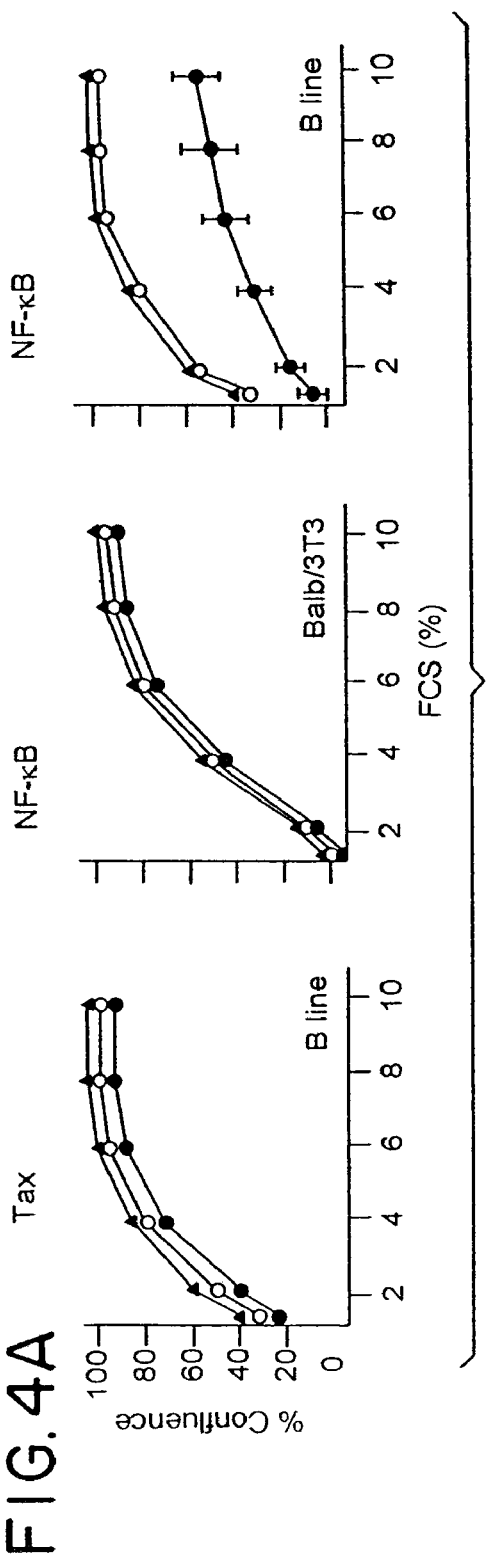
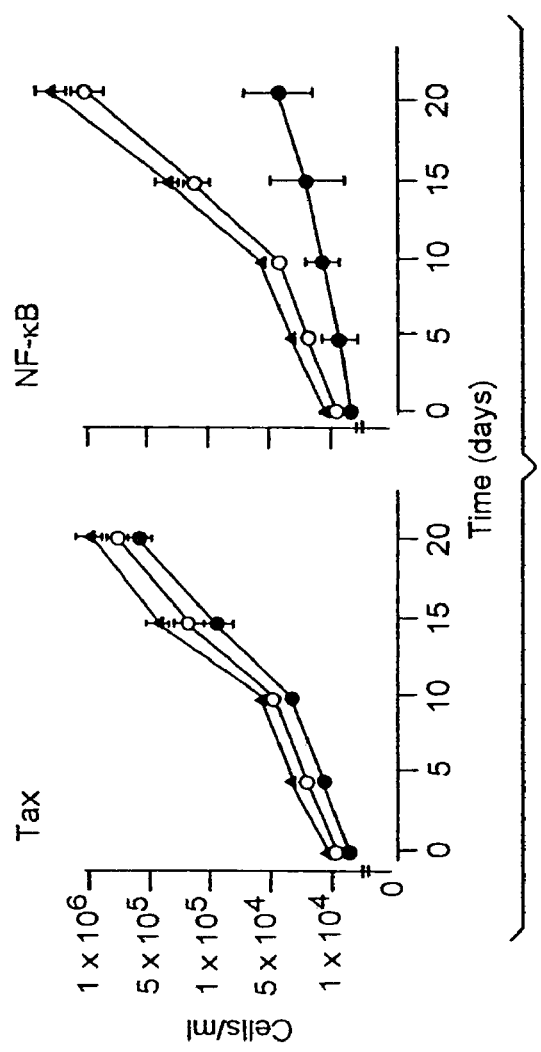
FIG. 4A
FIG. 4B

Sense

Antisense

SUPPRESSION OF NUCLEAR FACTOR-κB DEPENDENT PROCESSES USING OLIGONUCLEOTIDES

CROSS REFERENCE TO RELATED APPLICATION(S)

This application is a continuation application of U.S. application Ser. No. 11/888,342, filed Jul. 30, 2007, which is a continuation application of U.S. application Ser. No. 10/328,861, filed Dec. 24, 2002, now issued as U.S. Pat. No. 7,268,121; which is a continuation application of U.S. application Ser. No. 08/110,161, filed Aug. 20, 1993, now issued as U.S. Pat. No. 6,498,147; which is a continuation-in-part application of U.S. application Ser. No. 07/887,331, filed May 22, 1992, now abandoned. The disclosure of each of the prior applications is considered part of and is incorporated by reference in the disclosure of this application.

GRANT INFORMATION

This invention was made with Government support under Grant Nos. CA 50234 and MH 47680 awarded by the National Institutes of Health. The United States government has certain rights in this invention.

BACKGROUND OF THE INVENTION

1. Field of the Invention

This invention relates generally to methods and compositions useful in inhibiting disorders dependent upon expression of the inducible transcription factor NF-κB.

2. Background Information

The NF-κB transcription activator is a multiprotein complex which can rapidly induce the synthesis of defense and signalling proteins upon exposure of cells to a wide variety of mostly pathogenic agents. Three protein subunits, κB, p50, and p65, control the biological functions of NF-κB. IκB is a 35-43 kDa subunit which inhibits the DNA-binding of NF-κB and serves to retain NF-κB in an inducible form in the cytoplasm of unstimulated cells. Upon stimulation of cells, IκB dissociates from the inactive complex with p65 and p50. The released p50-p65 complex can then migrate into the nucleus and potently transactivate genes.

p50, one of the two DNA-binding submits of NF-κB, serves to recognize the more highly conserved half site in decameric sequence motifs with the consensus sequence GGGRNNYYCC. p50 has homologies to the rel and dorsal proteins, both of which are also involved in cytoplasmic/nuclear signalling, and is identical to factors known as KBF1, H2TF1 and EBP-1. p50 is synthesized as an inactive precursor of 110 kDA.

The other DNA binding subunit, p65, binds to the less conserved half site of κB motifs and is apparently also homologous to rel/dorsal proteins. The combination of p50 and p65 DNA binding subunits in NF-κB extends the repertoire of binding motifs recognized with high affinity. Only p65 appears to bind IκB. The inducibility of NF-κB is thus equally dependent on the presence of p65 as of UB. The NF-κB system is so far unique among transcription factors in that the interaction of three distinct subunits control multiple regulatory characteristics of a transcription activator including the subcellular localization and the activity, inducibility, and specificity of DNA binding.

Many different binding sites for NF-κB have been characterized and for most the base requirements for protein binding have been defined by methylation interference analysis or other footprinting techniques (Baeuerle, *Biochem Biophys. Act,* 1072:63.1991). Most binding sites are decameric, but some are undeca- or dodecameric. The latter may arise from NF-κB binding in a mutually exclusive manner to two or three decameric motifs within the longer sequences. An alternative explanation is that p50-p65 or the p50 dimer can contact 10, 11 or even 12 base pairs. Support for the latter hypothesis comes from mutational analysis of the enhancer of the MHC class I gene H-2 $K^b$.

Among those disorders which are linked to activation of NF-κB is leukemia caused by the retrovirus HTLV-1. Human T-cell leukemia virus (HTLV-1) is recognized as the etiologic agent of the human malignancy, adult T cell leukemia (B. J. Poiesz, *Proc. Natl. Acad. Sci. USA,* 77:7415, 1980; D. J. Slamon, et al., *Science,* 226:61, 1984; W. C. Goh, et al., *ibid* 227:1227, 1985).

Circumstantial data has implicated the HTLV-I encoded tax gene in leukemo-genesis. This gene encodes a 40 kD protein that causes transcriptional transactivation of viral gene expression and also activates expression of certain cellular genes that are important for growth (A. J. Cann, et al., *Nature* 318:571, 1985; B. K. Felber, et al., *Science,* 229:675, 1985; J. Fujisawa, et al., *Embo Journal* 5:713, 1986). In vitro studies have demonstrated that tax can activate the promoters of the interleukin 2 receptor (IL-2R) a-chain, GM-CSF, fos, PDGF, IL-6, NGF, TGF-β, HIV LTR as well as its own LTR (D. J. Slamon et al., *Science,* 226:61, 1984; W. C. Goh et al., *ibid,* 227:1227, 1985; J. Inoue, et al., *Embo Journal* 5:2883, 1986; S. Miyatake, et al., *Mol. Cell. Biol.* 8:5581, 1988; K. Nagata, et al., *J. Virol.* 63:3220, 1989; L. Ratner, *Nucleic Acid Research,* 17:4101, 1989; J. Sodroski, et al., *Science,* 228: 1430, 1985; J. E. Green, et al., *Mol. Cell. Biol.* 11:4635, 1991; S. J. Kim, et al., *J. Exp. Med.,* 172:121, 1990; E. Bohnlein, et al., *J. Virol.,* 63, 1578, 1988). In vitro studies of tax effects on gene expression, have demonstrated two independent pathways for its action on transcription (M. R. Smith and W. C. Green, *J. Clin. Invest.* 87:761, 1991). The first affects the family of nuclear transcription factors related to c-rel which bind to NF-κB sites and are important for the normal activation of lymphocytes. NF-κB response sequences occur in a number of genes including the HIV LTR (G. Nable, et al., *Nature* London, 326:711, 1987) and the IL-6 promoter (T. A. Libermann, et al., *Mol. Cell. Biol.,* 10:2327, 1990). The heterodimer composed of the p50 and p65 rel related proteins have been shown to affect the transcription of many of these genes (P. A. Baeuerle, *Biochem. Biophys. Acta,* 1072:63, 1991). The other effect of tax is thought to be NF-κB independent, whereby tax activates its own promoter through three tax responsive elements (TREs). Similar sequence motifs have been identified in fos (M. Fujii et al., *Proc. Natl. Acad. Sci. USA,* 85:8526, 1988), an immediate early response gene.

Unfortunately, although it is known that tax and other disorders appear linked to activation of NF-κB, no therapeutic modalities exist which can suppress this activation and thereby inhibit progression or establishment of the disorder. The present invention addresses this need and provides composition and means of accomplishing this goal.

SUMMARY OF THE INVENTION

The present invention arose from the discovery that an antisense oligonucleotide which hybridizes to nuclear factor-κB (NF-κB) mRNA can be used to suppress processes which depend upon activation of NF-κB.

As a consequence of this discovery, the present invention represents a major improvement over existing techniques for suppressing NF-κB dependent processes which often entail use of chemicals which are highly toxic, especially in terms of their utilization in vivo. The antisense oligonucleotides of the invention display a high degree of biocompatibility with host systems such that the low efficiency and toxic aspects of prior art methodologies and compositions is avoided.

BRIEF DESCRIPTION OF THE DRAWINGS

FIG. 4 is growth curves of cells treated with tax or NF-$_K$B antisense, in vitro. Symbols are mock (No; >), sense (SEN; □) and antisense (ANT; X).

DESCRIPTION OF PREFERRED EMBODIMENTS

Figure 1A:
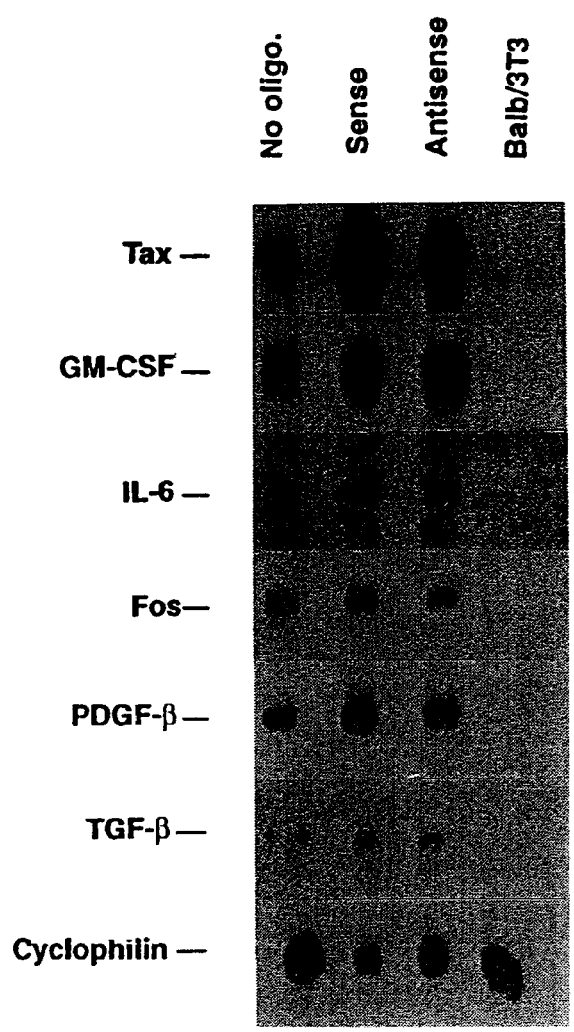
FIG. 1A, B is a Northern analysis of early genes in tax or NF-κB antisense treated cells.

The present invention relates to an antisense oligonucleotide sequence which can hybridize to nuclear factor κB (NF-κB) subunit mRNA. This antisense sequence is highly useful for suppressing in vitro or in vivo NF-κB dependent or associated processes in individuals. Such processes are typically associated with such disorders as those mediated by immune or cytokine responses (for example, septic shock) as well as those disorders induced by infectious agents such as retroviruses, more specifically, HIV and HTLV.

The antisense oligonucleotides of the invention are preferably directed to the p65 or p50 subunits NF-κB mRNAs. Most preferably, the antisense oligonucleotides are complementary to the translation initiation nucleic acid sequence of these subunits. In general, the antisense oligonucleotides of the invention are capable of hybridizing to DNA which has the nucleotide sequence 5'-ATCTTCACCATGGCAGACGAT-3' (hu p50)(SEQ ID NO:1) or 5'-CGGCCATGGACGAACT-GTTC-3' (hu p65)(SEQ ID NO:2) or 5'-ATCTTCACCATG-GCAGACGA-3' (mus P50)(SEQ ID NO:3) or 5'-TGAC-CATGGACGATCTGTTT-3' (mus p65)(SEQ ID NO:4). Most preferred are antisense oligonucleotides having the nucleotide sequence: 5'-ATCGTCTGCCATGGTGAAGAT-3' (hu p50 AS)(SEQ ID NO:5) or 5'-GAACAGTTCGTC-CATGGCCG-3' (hu p65 AS)(SEQ ID NO:6) or 5'-TCGTCT-GCCATGGTGAAGAT-3' (ms p50 AS)(SEQ ID NO:7) or 5'-AAACAGATCGTCCATGGTCA-3' (ms p65 AS)(SEQ ID NO:8) where hu=human and mus=murine.

As a general matter, the oligonucleotide employed will have a sequence that is complementary to the sequence of the target RNA. However, absolute complementarity is not required; in general, any oligonucleotide having sufficient complementarity to form a stable duplex with the target RNA so that translation of the RNA is inhibited, is considered to be suitable. Since stable duplex formation depends on the sequence and length of the hybridizing oligonucleotide and the degree of complementarity between the antisense oligonucleotide and the target sequence, the system can tolerate less fidelity (complementarity) when longer oligonucleotides are used. However, it is presently believed that oligonucleotides of about 8 to 40 bases in length and having sufficient complementarity to form a duplex having a melting temperature of greater than about 40° C. under physiologic conditions are particularly well suited for practice of the invention (Thoung, et al., *PNAS USA,* 84:5129, 1987; Wilson, et al., *Nucleic Acids Res.,* 16:5137, 1988). Accordingly, such oligonucleotides are preferred.

Another variable that may affect practice of the invention is the region of the target RNA to which the selected oligonucleotide is designed to hybridize. Although oligonucleotides capable of stably hybridizing with any region of the RNA may be suitable for practice of the invention, oligonucleotides complementary to a region including the translation initiation nucleic acid sequence of the NF-κB subunit are particularly effective. The antisense oligonucleotide is considered effective as long as the translation of the mRNA to which the oligonucleotide is complementary is inhibited.

The oligonucleotide employed may be unmodified or modified. Suitable modifications include, but are not limited to, the ethyl or methyl phosphonate modifications disclosed in U.S. Pat. No. 4,469,863 and the phosphorothioate modifications deoxynucleotides described by LaPlanche, et al. (*Nucleic Acids Research* 14:9081, 1986), and by Stec. et al., (*J. Am. Chem. Soc.* 106:6077. 1984). The modification to the antisense oligonucleotide is preferably a terminal modification in the 5' or 3' region. Preferred are modifications of the 3' terminal region as described herein. Furthermore, recent advances in the production of oligoribonucleotide analogues mean that other agents may also be used for the purposes described here, for example, 2'-methylribonucleotides (Inoue, et al., *Nucleic Acids Res.* 15:6131, 1987) and chimeric oligonucleotides that are composite RNA-DNA analogues (Inoue, et al., *FEBS Lett.,* 215:327. 1987).

Of course, in order for the cell targets to be effectively inhibited by the selected antisense oligonucleotides, the cells must be exposed to the oligonucleotides under conditions that facilitate their uptake by the cells. For in vitro therapy this may be accomplished by a number of procedures, including, for example, simple incubation of the cells with the oligonucleotides in a suitable nutrient medium for a period of time suitable to achieve selective inhibition of the cells. For example, where the cell targets of the antisense oligonucleotide of the invention are present in bone marrow cells, procedures can be employed such as those described by Gartner and Kaplan, *Proc. Natl. Acad. Sci. USA,* 77:4756, 1980; Coulombel, et al., *Blood* 67:842, 1986; Meagher, et al., *Blood,* 72:273, 1988; or U.S. Pat. No. 4,721,096 with an optimal concentration of the selected antisense oligonucleotide. After the marrow cells have been exposed to the oligonucleotide and, in some cases, cultured as described above, they are then infused into the transplant recipient to restore haemopoiesis.

The antisense oligonucleotide of the invention can also be administered to provide in vivo therapy to a patient having a disorder which is associated with activation of NF-κB. Such therapy can be accomplished by administering, in vitro and in vivo as the case may be, a therapeutically effective amount of antisense oligonucleotide, or as further described below, the antisense oligonucleotide in combination with glutathione precursor. The term "therapeutically effective" means that the amount of antisense oligonucleotide administered alone, or in combination with glutathione precursor, is of sufficient quantity to suppress to some beneficial degree activation of NF-κB and the disorder associated with activation of NF-κB. Examples of such disorders include those associated with LPS-induced septic shock and those associated with elevated IL-6 production. The NF-κB process may also be tissue specific. For example, the disorder may be detected in the spleen, liver, kidney, or lung. Preparations utilizing antisense oligonucleotide can comprise the oligonucleo-tide in a simple buffer solution or, alternatively, in a more complex vehicle as described below.

The invention also provides a method of monitoring the effectiveness of suppressing NF-κB and NF-κB dependent processes in the tissue of an individual after administering a therapeutically effective amount of NF-κB antisense comprising detecting the level of cytokine production in a tissue, before and after antisense therapy. Preferably, the cytokine is IL-6. IL-6 can be detected by immunological methods such as ELISA, or nucleic acid methods, such as Northern blot analysis of IL-6 mRNA.

Studies have suggested that glutathione precursors may be useful in regulating activation of NF-κB (Staal, et al., *Proc. Natl. Acad. Sci. USA, §7*:9943, 1990; Bruno, et al., *Biochemical Pharmacology,* 37:4319, 1988). Typically, these precursors are an acylcysteine, such as N-acetylcysteine. These compounds appear to block activation of NF-κB in both resting as well as activated cells. Unfortunately, these compounds have been found to be extremely toxic in vivo when administered alone. An advantage of the present system is that it allows a means of reducing the concentration of glutathione precursors which is utilized by combining the precursor with the antisense oligonucleotide of the invention. Thus, according to the method of the invention, it is possible to administer the antisense oligonucleotide in combination with a precursor of glutathione. The term "in combination" means that the antisense oligonucleotide and the glutathione precursor are administered (1) separately at the same or different frequency using the same or different administration or (2) together in a pharmaceutically acceptable composition. If desired, the antisense oligonucleotide and glutathione precursor can be administered substantially contemporaneously. The term "substantially contemporaneously" means that the antisense oligonucleotide and glutathione precursor are administered reasonably close together with respect to time, for example, simultaneously to within a few hours.

"Pharmaceutical combination" includes intimate mixtures of the two components of the invention, as in classical compositions, and also non-mixed associations, such as those found in kits or pharmaceutical packs.

Antisense oligonucleotide, alone or in combination with glutathione precursor, can be administered in a single dose or can be administered in multiple doses over a period of time, generally by injection. Various administration patterns will be apparent to those skilled in the art. The dosage ranges for the administration of the antisense obigonucleotide of the invention are those large enough to produce the desired effect of suppressing the undesired NF-κB dependent process. The dosage should not be so large as to cause adverse side effects, such as unwanted cross-reactions, anaphylactic reactions, and the like. Generally, the dosage will vary with the age, condition, sex and extent of the disease in the patient and can be determined by one of skill in the art without undue experimentation. The dosage can be adjusted by the individual physician in the event of any counter indications, immune tolerance, or similar conditions. Those of skill in the art can readily evaluate such factors and, based on this information, determine the particular therapeutically effective concentration of antisense oligonucleotide, or antisense oligonucleotide in combination with glutathione precursor, to be used. Generally, dosage for antisense oligonucleotide can vary from about 1.0 mg/g body weight to about 100 mg/g body weight, preferably from about 10 mg/g body weight to about 80 mg/g body weight, most preferably from about 30 mg/g to about 50 mg/g body weight. Glutathione precursor, such as N-acetylcysteine, can be administered from about 1 mM to about 50 mM, more preferably from about 10 mM to about 40 mM, most preferably from about 20 mM to about 30 mM.

Antisense oligonucleotide and glutathione precursor can be administered as the compound or as a pharmaceutically acceptable salt of the compound, alone, in combination, or in combination with pharmaceutically acceptable carriers, diluents, and vehicles. Most preferably, antisense oligonucleotide and glutathione precursor are mixed individually or in combination with pharmaceutically acceptable carriers to form compositions which allow for easy dosage preparation.

The antisense oligonucleotide and glutathione precursor composition of the present invention can be administered in any acceptable manner including by injection, using an implant, and the like. Injections and implants are preferred because they permit precise control of the timing and dosage levels used for administration, with injections being most preferred. Antisense oligonucleotide and glutathione precursor compositions according to the present invention are preferably administered parenterally.

Antisense oligonucleotide according to the present invention can be administered to the patient in any acceptable manner including orally, by injection, using an implant, nasally and the like. Oral administration includes administering the composition of the present invention in tablets, suspensions, implants, solutions, emulsions, capsules, powders, syrups, water compositions, and the like. Nasal administration includes administering the composition of the present invention in sprays, solution, and the like. Injections and implants are preferred because they permit precise control of the timing and dosage levels used for administration, with injections being most preferred. Antisense oligonucleotide is preferably administered parenterally.

Glutathione precursor according to the present invention can be administered to the animal in any acceptable manner including by injection, using an implant, and the like. Injections and implants are preferred because they permit precise control of the timing and dosage levels used for administration, with injections being most preferred. Glutathione precursor is preferably administered parenterally.

Antisense oligonucleotide and glutathione precursor compositions can be administered in an injectable formulation containing any glutathione precursor and antisense oligonucleotide compatible and biocompatible carrier such as various vehicles, adjuvants, additives, and diluents to achieve a composition usable as a dosage form.

Aqueous vehicles such as water having no nonvolatile pyrogens, sterile water, and bacteriostatic water are also suitable to form injectable antisense oligonucleotides and glutathione precursor formulations. In addition to these forms of water, several other aqueous vehicles can be used. These include isotonic injection compositions that can be sterilized such as phosphate buffered saline, sodium chloride, Ringer's, dextrose, dextrose and sodium chloride, gelatin and lactated Ringer's. Addition of water-miscible solvents, such as methanol, ethanol, or propylene glycol generally increases solubility and stability of the compounds in these vehicles.

Nonaqueous vehicles such as cottonseed oil, squalene, sesame oil, or peanut oil and esters such as isopropyl myristate may also be used as solvent systems for glutathione precursor and antisense oligonucleotides. Additionally various additives which enhance the stability, sterility, and isotonicity of the composition including antimicrobial preservatives, antioxidants, chelating agents, gelatin and buffers can be added. Any vehicle, diluent; or additive used would, however, have to be compatible with the compounds of the present invention.

Antisense oligonucleotides and glutathione precursor compositions according to the present invention can be administered in the form of a slow-release subcutaneous implant which is inserted beneath the skin. The implant can take the form of a pellet which slowly dissolves after being implanted or a biocompatible and glutathione precursor and antisense oligonucleotide compatible delivery module well known to those skilled in the art. Such well known dosage forms are designed such that the active ingredients are slowly released over a period of several days to several weeks.

The following examples are intended to illustrate but not limit the invention. While they are typical of those that might be used, other procedures known to those skilled in the art may alternatively be adopted without resort to undue experimentation.

EXAMPLE 1

Antisense Inhibition of Tumor Cells In Vitro

A. Preparation of Oligonucleotides

Sense and antisense oligodeoxynucleotides (ODNs) were synthesized by the phosphoramide method on an ABI automated synthesizer (Foster City, Calif.). The phosphothioate (PS) sulfurization modification (Stein, et al., *Nucleic Acids Res.*, 16:3209, 1988) was performed during synthesis, where TETD and acetonitrile were substituted for the usual iodine, pyridine and water during the oxidation step. ODNs were purified according to published procedures (Miller, et al., *J. Biol. Chem.*, 255:9659, 1980).

One set of sequences was selected to be complementary to the transcript encoded by the HTLV-I LTR-tax cassette which had previously been used to generate transgenic mice (Nerenberg, et at., *Science*, 237:1324, 1987). The antisense sequence was GAAGTGGGCCATGTGGA*A*G (SEQ ID NO:9) (location 718-737 on HTLV-I LTR-tax construct) which included the AUG initiation codon (underlined) and sense sequence was CTTCCACATGGCCCACT*T*C* (SEQ ID NO:10), the exact complement of the tax-antisense ODN above. Asterisks show sites of PS modification.

An upstream sense primer (AAGCGTGGAGACAGT-TCAGG, (SEQ ID NO:11) location 423-442) was synthesized as a primer pair for the modified or unmodified antisense primer (location 737-718). Similarly, a downstream antisense oligonucleotide (TTGGCGGGGTAAGGAC-CTTG, (SEQ ID NO:12) location 986-1004) was synthesized to pair with the modified or unmodified sense (location 718-737).

A second set of ODNs was prepared based on the nucleotide sequences of the p50 and p65 subunits of NF-κB. The ODNs for p50 NF-κB were the following: (AS=antisense; S=sense) 5'-ATCGTCTGCCATGGTCAAGAT-3' (AS human)(SEQ ID NO:5), 5'-TCGTCTGCCATGGTGAA-GAT-3' (AS mouse)(SEQ ID NO:7), 5'-ATCTTGACCATG-GCAGACGAT-3'(S human)(SEQ ID NO:1) and 5'-ATCT-TCACCATGGCAGACGA-3' (S mouse)(SEQ ID NO:3). The corresponding ODNs for p65 were: 5'-GAACAGT-TCGTCCATGGCCG-3' (AS human)(SEQ ID NO:6), 5'-AAACAGATCGTCCATGGTCA-3' (AS mouse)(SEQ ID NO:8), 5-'CGGCCATGGACGAACTGTTC-3' (S human) (SEQ ID NO:2), and 5'-TGACCATGGACGATCTGTTT-3'(S mouse)(SEQ ID NO:4). Initiation codons are underlined. Both sets of ODNs extended over the translational initiation sites of NF-κB mRNAs.

B. Establishment of Tax Expressing Tumor Cell Lines

LTR-tax transgenic mice were originally generated from CD1 females and (C57BL/6×DBA/2) F1 males, and thus were genetically highly heterogeneous (Nerenberg, et al., *Science,* 237:1324, 1987). One line (6-2) containing 40 copies of the transgene and expressing high levels of tax was back bred to C57BL/6 mice for greater than 30 generations. Spontaneously arising fibroblastic tumors were sterily harvested, finely minced and grown in bulk culture for 30 passages. Single cell clones were obtained by dilution and growth in Terasaki plates in the presence of filtered conditioned medium from the bulk cultures. Individual clones were grown in bulk culture and tested for ability to form tumors in syngeneic animals. One of these lines (designated B line) was selected for further study as it rapidly and reproducibly caused tumors when innoculated into the hind limb of animals when $1 \times 10^6$–$1 \times 10^7$ cells were injected. Tumors grew rapidly at the site of local injection and never caused metastasis. These tumors attracted high numbers of granulocytes, similar to the original tumors (Nerenberg, et al., *Science,* 237:1324, 1987), presumably caused by high secretion of cytokines. Mice typically die from localized effects of the tumor by 2 months after injection. Other cell lines had similar gene expression phenotypes, but grew more slowly, or required higher numbers of inoculated cells to form tumors. Cells were $H-2^B$ haplotype, and expressed high levels of tax.

C. Effect of Oligonucleotides on Tumor Cells In Vitro

Cells of the B line were cultured in T-75 flasks to 70% confluence. Cells were grown in modified DMEM (Cellgro, Mediatech, Washington, DC) plus 10% heat inactivated fetal calf serum (FCS)(GIBCO, Grand Island, N.Y.) except where indicated. The unmodified or PS modified ODNs were added to a final concentration of 20 μg/cc for 48 hrs. The cells were pre-incubated for 6 hrs in the presence of these ODNs with 10% FCS or without serum prior to transfections. Poly A+ RNA was extracted from tissues and digested with proteinase K and purified by the FastTrack method (Bradley, et al., *Bio-Techniques,* 6:114, 1988)(Invitrogen, San Diego, Calif.). Samples were denatured and run on formaldehyde 1.4% agarose gels followed by blotting onto nylon membrane and UV fixation. Cloned cDNAs (early genes) were used for generation of probes. Probes were labeled via the random primer method with $^{32}$P dATP plus dCTP. Specific activities were $1 \times 10^9$ cpm/μg. The effect of antisense on tax or NF-κB/gene expression in vitro is shown by Northern analysis in FIGS. 1, A and B, respectively.

Tax specific sense ODNs used as a control, had no effect on cell growth or gene expression (FIG. 1A lane 2). Previous analyses of tax antisense ODN treated cells demonstrated approximately 10 fold decrease in tax protein production, which led to a corresponding 10 fold decrease in transactivation of the HTLV-I LTR in transient assays. A specific decrease in the levels of specific RNA can be seen, and this is consistent with direct (CRE/ATF) activation of this promoter by tax (Fujii, et al., *Proc. Natl. Acad. Sci.,* 85:8526, 1988). However, no alteration in the levels of many other growth related genes was seen (FIG. 1A lane 3), suggesting that they were not directly activated by tax.

Figure 1B:
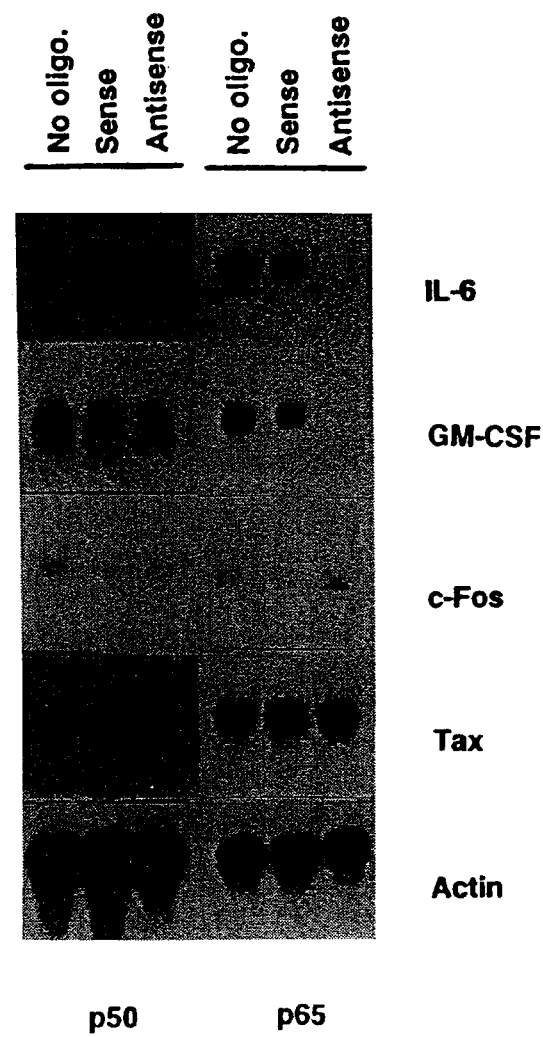

In contrast, inhibition of either the p50 or p65 subunits of NF-κB caused profound effects on endogenous cytokine gene expression (FIG. 1B). IL-6 was affected more than GM-CSF and there was no apparent effect on c-fos, tax, or actin expression. Inhibition of p65 was slightly more effective than p50. This result demonstrated specificity of the ODNs for the NF-κB responsive genes. To quantitate functional effects of this inhibition, transient CAT expression assays were performed on an NF-κB dependent promoter. The plasmid HIV-CAT was used, as this retroviral LTR contains 2 copies of an NF-κB target sequence and has shown to be highly NF-κB responsive (Nabel, et al., *Nature,* 326:711, 1987).

Figure 2:
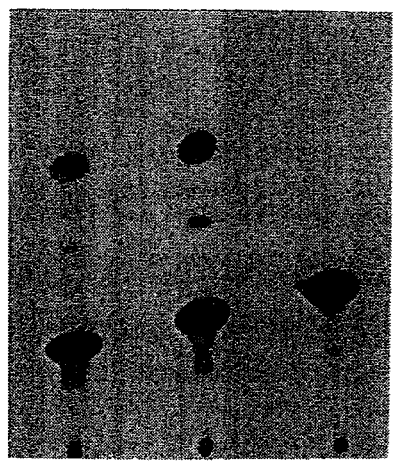
FIG. 2 is a CAT assay in the presence of NF-κB p65 antisense ODNs.

FIG. 2 shows greater than 20 fold inhibition of CAT expression in the presence of NF-κB p65 antisense ODNs. In these studies, cells (cell line B) were pretreated with p65 NK-κB oligonucleotides for 8 hours. The cells were then transfected with 5 μg of an HIV LTR-CAT construct. CAT activity was analyzed after an additional 48 hours. As an internal control, 5cfig of CMV-β gal (Clontech, San Francisco, Calif.) was co-transfected and analyzed by MUG assay (MacGregor, et al., *Methods in Molecular Biol.,* 1989). Transfections used Lipofectin (Bethesda Research Laboratories, Bethesda, Md.) as per Flegner, et al., *Proc. Natl. Acad. Sci.* 85:7413, 1989). The level of CAT activity was determined by thin layer chromatography using $^{14}C$ chloramphenicol. Results were quantitated by scintillation counting of the extracted radiographic spots and are shown.

Figure 3:
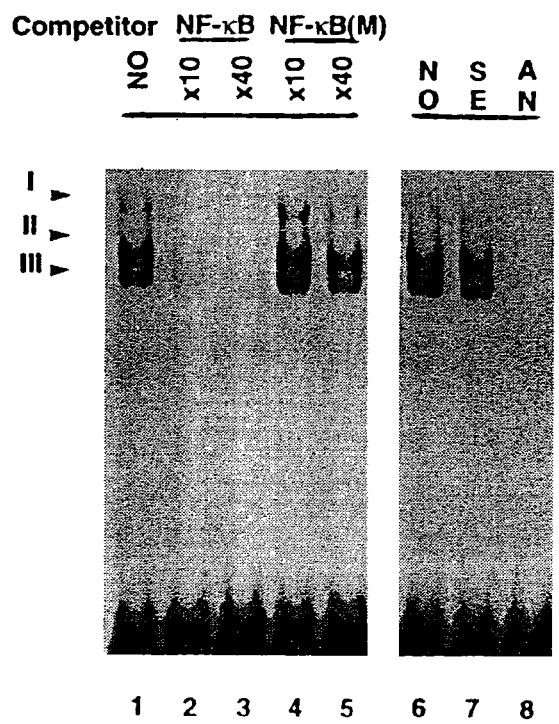
FIG. 3 is an electrophoretic mobile shift assay (EMSA) of nuclear extracts obtained from unmanipulated, sense and antisense treated cells.

The findings above were further confirmed by direct assay of protein binding to NF-κB target sites. Electrophoretic mobility shift analysis (EMSA) of nuclear extracts obtained from unmanipulated, sense and antisense treated cells are shown in FIG. 3.

The target sequence for EMSA consisted of a double stranded 35-mer: 5'- AGCTFCAACAGAGGGGACTTTC-CGAGAGGCTCGAG-3' (ODN A)(SEQ ID NO:13). The underlined sequence is identical to the NF-κB consensus in mouse Ig k light chain and to that used by N. Kabrun, et al., *Proc. Natl. Acad. Sci.,* 88:1783, 1991. The second strand was synthesized by hybridization with an 11-mer (ODN B), (complementary to the sequence not underlined) which was labeled at its 3' end by klenow mediated extension in the presence of á-$^{32}P$ dATP. This yielded a double stranded labeled 35-mer. The sequence for the mutant NF-κB was generated from a 35-mer (ODN c) sequence: 5'-AGCT-TCAACGAGGGACTTTCCGAGAGGCTCGAGC-3' (SEQ ID NO: 14). The NF-κB site is underlined with the mutation in small letters. This ODN was hybridized with ODN B and filled using klenow in the presence of unlabeled dNTPs.

For these experiments, 3 μg of nuclear extract from untreated (no), sense treated (se), or antisense treated (an) cells (cell line B) were incubated with a double stranded ODN encoding the NF-κB consensus target sequence (Kabrun, et al., *Proc. Natl. Acad. Sci.,* 88: 1783, 1991). $1 \times 10^4$ cpm (approx. 0.86 ng) of labeled ODN was used. Procedures were as published (Kabrun, et al., *Proc. Natl. Acad. Sci.,* 88: 1783, 1991). Three NF-κB specific bands (I, II, III)(Baldwin, et al. *Mol. Cell. Biol.,* 11:4943, 1991) were readily identified. Competition assays are shown in the left panel. The ratios of molar excess of unlabeled consensus ODN (NF-κB) or mutant NF-κB(M) are shown.

Analysis of unmanipulated cells (lanes 1,6) revealed 3 bands of NF-κB complexes similar to those previously described (A. Baldwin, et al., *Mol. Cell. Biol.,* 11:4943, 1991). Unlabeled NF-κB consensus oligonucleotide competitively inhibited all complexes (lanes 2,3). In contrast, an oligonucleotide with a single G to C substitution in the binding site failed to block the formation of complexes (lanes 4,5). These data confirm the specificity of this EMSA assay for detection of NF-κB complexes. Treatment of these cells with p65 sense ODNs had no effect on complex formation (lane 7). In contrast, use of p65 antisense ODNs specifically ablated all complex formation (lane 8). This occurred in a dose dependent manner and was also obtained with p50 specific ODNs (data not shown).

The effects of tax or NF-κB antisense ODN inhibition on in vitro growth of mouse cell lines are shown in FIG. 4A. Balb/3T3 cells, or cell line B were cultured in 10 cm dishes, in the presence of varying concentrations of FCS (as indicated on the abscissa). $1 \times 10^4$ cells/ml were plated, an amount calculated to give approximately 30% confluence. 20 μg/ml p65 sense or antisense ODNs were added and cultures were allowed to grow for 6 days. ODNs were replenished at 3 day intervals. Cells were counted and expressed as % confluence. Mock treatment (No; >), sense (SEN; O) and antisense (ANT; •) are indicated. For each cell line, mock, sense and antisense PS ODN treatments were performed. A constant amount of ODN (20 μg/ml) was used, and growth rates were measured daily. The data in FIG. 4 shows the percent confluence at day 6 as a function of varying serum concentration. Serum concentration has profound effects on the growth rate of cells and previous studies have demonstrated induction of nuclear translocation of NF-κB by serum (T. A. Libermann, et al., *Mol. Cell. Biol.,* 10:2327, 1990). Therefore, this allowed the effects of ODNs to be displayed over a wide range of growth conditions. Treatment with tax specific ODNs, which caused a 90% inhibition of tax expression, had no apparent effects on growth rates of cells. In contrast, p65 antisense ODNs had profound effects on the growth of cell line B, with no apparent effect on Balb/3T3 growth at all serum concentrations. Similar results were obtained when the concentration of NF-κB ODN was varied and serum concentration was fixed, or with other tax expressing fibrosarcoma lines. p50 ODNs were slightly less effective at the same concentration but gave a similar profile. Mixtures of both p50 and p65 ODNs had an additive inhibitory effect.

It is likely that additional HTLV-I encoded proteins other than tax are necessary for transformation by the native virus. Thus, tax and NF-κB may play different roles in maintenance of transformation of human lymphocytes than that demonstrated for mouse fibroblasts. To determine the effects of tax and NF-κB antisense ODNs on lymphocytes, the HTLV-I transformed human cell line, MT2 (M. Kozac, *Nature,* 308: 241, 1984) was analyzed. FIG. 2B shows a profile of growth inhibition similar to that seen for the HTLV-I transformed murine cell line MT-2 (Kozac, *Nature,* 308:241, 1984). Cells were grown in 4% FCS in the presence or absence of NF-κB or tax ODNs. Synthesis of new PS ODN was required, as the 5' end of the tax translation initiation target sequence in the transgenic mice varied slightly from that in the native human virus. (The sequence for inhibition of tax in human cells is antisense 5'-TCGTCTGCCATGGTGAAGAT-3' (SEQ ID NO:7).) Cells were allowed to grow for up to 20 days. Growth is expressed as absolute cell number in triplicate 6 well dishes. Tax antisense ODNs had no apparent effect on growth of the infected human cell line (left panel), despite significant inhibition of tax protein. In contrast, p65 antisense ODNs profoundly inhibited growth at all time points.

EXAMPLE 2

Antisense Inhibition of Tumor Growth In Vivo

Figure 5A:
FIG. 5 shows in vivo growth inhibition of B cell line tumors by NF-κB antisense treatment.
Figure 5B:

Studies were performed on the effects of ODN mediated suppression of unmanipulated line B cells which were transferred to syngeneic C57B1/6 mice. Once tumors were established (7 days after injection in the hind limb), mice were treated with 3 intraperitoneal (IP) injections at 3 day intervals of 40 µg/g of sense and antisense ODNs as described by Goodchild, et al. (T. A. Libermann, et al., *Mol. Cell. Biol.*, 10:2327, 1990). Western blot analysis of tumors exposed to tax antisense ODN treatment showed virtually complete suppression of tax expression at the 40 µg/g dose. As previously seen above in in vitro studies, no perturbation in growth rate of tumors was seen in the animals treated with tax antisense ODNs. Treatment with antisense ODN to NF-κB had dramatically different effects. FIG. 5 shows a typical comparison of typical matched mice either 15 days after treatment with sense (left) or antisense (right) ODNs to p65. In each case, treatment with antisense to p65 caused regression of tumors, while treatment with sense caused no diminution in growth. A total of eight antisense treated and eight controls were analyzed over time, and growth rates were determined by weighing excised tumors. The results are shown in Table 1.

TABLE 1

TIME COURSE ANALYSIS OF NF-κB p65 SENSE AND ANTISENSE TREATED MICE

| DAYS AFTER START OF TREATMENT | TREATMENT | | |
|---|---|---|---|
| | NONE | SENSE | ANTISENSE |
| 0 | 348 ± 214[a] | N.D.[b] | N.D. |
| 4 | 799 ± 343 | 748 ± 424 | 260 ± 198 |
| 8 | 1385 ± 774 | 1264 ± 671 | 122 + 84 |
| 15 | 5394 ± 2864 | 4874 ± 2571 | 45 ± 28 |
| 60 | N.D. | 7243 ± 3872 | <45[c] |

[a]tumor weight without capsules (mg)
[b]not determined
[c]undetectable (less than 45 mg)

Clear growth inhibition was seen as early as 8 days after first treatment with profound differences occurring by 15 days. Histologic analysis of these tumors was also performed. Samples obtained from mice treated with sense NF-κB ODN revealed typical morphology characteristic of growing tumors. Treatment with antisense ODN showed focal tumor necrosis with inflammatory infiltrate by 4 days, followed by widespread segmental necrosis by 7 days. By 10 days, fibrotic tissue and tumor capsule with occasional inflammatory cells were all that remained. Beyond 10 days, it was difficult to identify the tumor site. Untreated mice, or those treated with sense ODNs, died between 8 and 12 weeks, while antisense ODN treated mice have been followed for up to 5 months without evidence of recurrence of tumors. In none of these mice were ODN injections given beyond the first 9 days.

The present studies reveal striking similarities between the effects of tax on mouse fibroblasts and HTLV-I or II virus on human T-cells. Though tax is necessary for transformation of mouse fibroblasts or human T-cells, the present studies indicate that continued high levels of tax expression (greater than 10% of the unmanipulated tumor) is not necessary for maintenance of the activated phenotype, or for growth of these cells. Similarly, HTLV-I associated human lymphomas frequently express very low levels of tax (T. Kinoshita, et al., *Proc. Natl. Acad. Sci. USA.*, 86:5620, 1989). In contrast, tumor growth is very sensitive to the levels of NF-κB expression. It appears that fully transformed mouse or human cells take up sufficient ODNs to effect tumor regression at doses of ODN which are well tolerated in vivo. In fact, previous toxicity studies suggest that mice readily tolerate at least 2.5 times amounts used here (J. Goodchild, et al., *Proc. Natl. Acad. Sci. USA.*, 85:5507, 1988). The basis for this difference in susceptibility of tax transformed and normal cells to NF-κB ODNs is unclear. It may represent a true difference in the requirement of intracellular NF-κB for survival. Alternatively, it may reflect a difference in the ability to internalize the ODNs. Previous studies have correlated the activation/growth state of cells with their ability to take up oligonucleotides (R. M. Crooke, *Anti-Cancer Drug Design*, 6:609, 1991; P. Iversen, ibid 6:531, 1991), and this process appears to occur via receptor mediated endocytosis. Tax or virus transformed tumor cells appear highly activated, which may cause them to take up more ODNs. Preliminary data supports this possibility.

Histologic analysis reported here showed profound and widespread tumor necrosis, and even this short window of treatment was apparently sufficient to prevent tumor recurrences. This suggests that these ODNs may provide a valuable approach to therapy of HTLV-I associated adult T-cell leukemia which has proved largely refractory to other modalities. In addition, these antisense sequences should be able to inhibit other processes which rely upon activation of NF-κB.

EXAMPLE 3

Antisense NF-κB ODNs Prevent LPS Mediated Death

Figure 6:
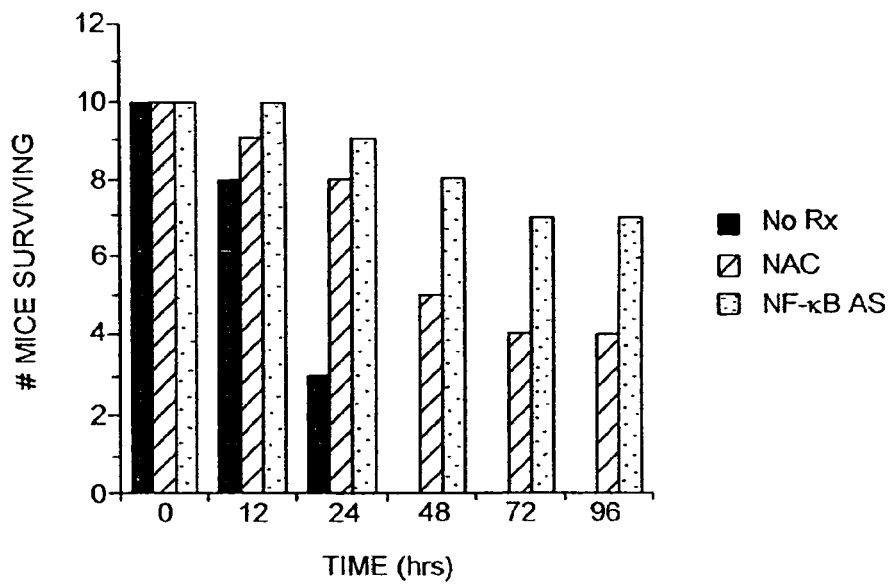
FIG. 6 shows the effect of antisense NF-κB antisense and N-acetyl cysteine (NAC) on mouse survival after LPS challenge.

In order to compare the effects of NAC or NF-κB AS-ODNs on the toxic manifestations of LPS induced septic shock, survival rates for the different treatment groups of mice were compared. This data is summarized in FIG. 6.

LPS-induced lethality. In vivo LPS challenge was performed according to the modified methods of Broner et al, *Critical Care Medicine* 16:848, 1988; and Peristeris, et al., *Cellular Immunology*, 140:390, 1992. A total of 35 C57Bl/6 mice (body weight 25-35 g) were studied in three treatment groups: 1)10 mice were treated with LPS followed by two mock injections of saline. 2) 10 mice were pretreated with NAC 12 hours and ½ hour prior to inoculation with LPS. 3) 10 mice were pretreated with NF-κB antisense ODNs 20 hours and ½ hour prior to LPS, and 5 mice were treated 20 and ½ hours prior to LPS with an irrelevant HTLV-I specific antisense ODN (Kitajima, I., et al., *J. Biol. Chem.* 267: 25881, 1992) as a control.

LPS (*Escherichia coli* 055:B5, Sigma, St. Louis., Mo.) was given as a single dose by intraperitoneal (ip) injection. Optimal results were obtained when a total dose of 100-150 mg (approx 5 mg/g body wt.) was administered in 0.3 ml of sterile, pyrogen-free saline. Qualtitatively similar results were obtained when sepsis was induced with 75 or 200 mg, with delayed or accelerated sickness, respectively. Two experiments were performed with 5 mice per group. NAC (Sigma, St. Louis. Mo.) was given intraperitonealy at a dose of 0.27 mg/g of body weight at a single site. Antisense NF-κB p65 ODN (sequence 5'-AAACAGATCGTCCATGGTCA-3' (SEQ ID NO:6)) was 3' terminal phosphorothioate (PS)-modified (Kitajima, I., et al., *Science* 259:1523, 1993; and Winer, B. J. 1971. Statistical Principles In Experimental Design. McGraw-Hill New York, N.Y.), as this has been shown to confer stability in animals (Kitajima, I., et al., *J. Biol. Chem.* 267:25881, 1992). Extensive previous experience with this ODN, in comparision with NF-kB sense and irrelevant antisense controls has shown it to be highly specific, both in vivo and in vitro (Kitajima, I., et al., *Science* 258:1792, 1992). The p65 AS ODN preserves this specificity even when used at doses twice the concentration used in this study. Antisense ODNs were administered ip at a dose of 40 mg/g of body weight, as it has been demonstrated that in previous in vivo studies (Kitajima, I., et al., *J. Biol. Chem.* 267:25881, 1992) this is an effective dose. AS-ODNs were administered i.p. in a volume of 0.3 ml sterile saline, while no treatment controls received only 0.3 ml of sterile saline. The number of surviving mice in each treatment group was recorded beginning at 12 hrs and additional observations were performed at 24, 48, 72 and 96 hours. The significance of differences in the survival rates between groups was evaluated by a Chi square test using all data points other than zero time. This provides an extremely conservative analysis in which a p value less than 0.05 is highly significant (Winer, B. J. 1971. Statistical Principles In Experimental Design. McGraw-Hill New York, N.Y.).

Control mice injected with LPS only, became ill within a few hours. This was manifested as decreased spontaneous activity, followed by hunching and decreased oral intake. Two of ten mice died by 12 hours and all of these mice ultimately died by 48 hours after a single intraperitoneal injection of 5 mg/g body wt (100-150 mg)(solid bars). Mice which were pretreated with NAC prior to LPS challenge showed increased but not significant protection from lethality (Total Chi Square 8.31, p=0.08), in agreement with previous studies (Peristeris, P., et al., *Cellular Immunology* 140:390, 1992; Broner, C. W., et al., *Critical Care Medicine* 16:848, 1988) (striped bars). Ultimate survival rate was 40% with one death occurring prior to 12 hours. Mice pre-treated with antisense NF-κB ODNs had a significantly better outcome (Total Chi square 11.86 p=0.018)(dotted bars). Deaths were delayed beyond 12 hours and the ultimate survival rate was 70%. Treatment with tax antisense or NF-κB sense control ODNs (Kitajima, I., et al., *Science*. 258:1792, 1992; Kitajima, I., et al., *J. Biol. Chem.* 267:25881, 1992) gave results identical to the untreated control.

EXAMPLE 4

Serum Levels of IL-6 are Decreased by NF-κB Antisense ODNs when Administered Prior to Septic Shock The results of Example 3 suggest NF-κB antisense inhibition dramatically reduces LPS induced lethality. In order to confirm that this is a specific consequence of NF-κB inhibition, the level of serum IL-6 was measured. Previous studies have demonstrated that IL-6 serves as an accurate indicator for NF-κB activation as this is a primary transcriptional activator of this cytokine (Liberman, T., et al., *Cell. Biol.* 10:2327, 1990). In addition, IL-6 is an important mediator of catastrophic immune responses such as inflammatory nephropathy (Horii, Y., et al., *J. Immunol.* 143:3949, 1989; Rugo, H. S., et al., *J. Clin. Invest.* 89:1032, 1992), may modulate immunoreactivity of tumors (Tabibzadeh, S. S., et al., *Am. J. Pathol.* 135:1025, 1989), and has been strongly implicated in the pathogenesis of septic shock (Ulich, T. R., et al., *J. Immunol* 146:2316, 1991; Troutt, A. B. et al., *J. Cellular Physiology,* 138:38, 1989).

Assay for IL-6 protein in serum. Sera from mice within each treatment group were obtained at 0, 1, 4, 8, and 20 hrs after LPS administration. Serum IL-6 was determined by an enzyme-linked immunosorbent assay (EUSA) according to the method of Pruslin et al. (Pruslin, F. H., et al., *J. Immunol. Method* 137:27, 1991) using rat anti-mouse monoclonal antibodies to IL-6 (Pharmingen, San Diego, Calif.). The detection limit for this assay was 100 pg/ml. Statistical differences between treatment groups were analyzed by the ANOVA test for time points beyond zero. Statistical analysis was performed using the program Statview, on a Macintosh computer.

Figure 7:
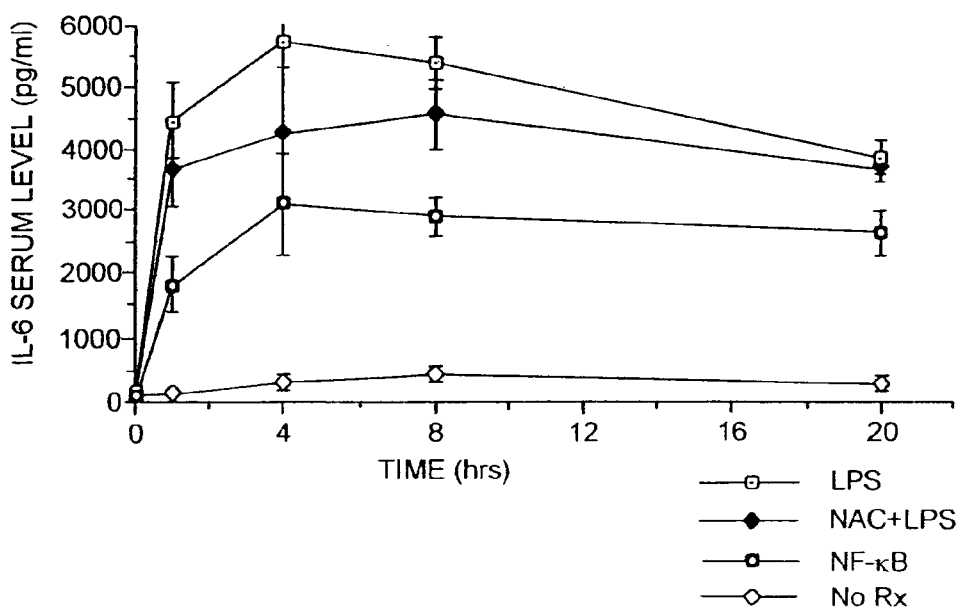
FIG. 7 shows serum IL-6 levels after LPS challenge. Error bars represent one standard deviation.

Serum IL-6 protein levels were measured by ELISA. Three mice were used per treatment group and experiments were repeated twice. Inter-experiment variability was less than 20%. Data were pooled from these experiments and are displayed in FIG. 7 (No Rx, LPS given at time zero without specific inhibitor. NAC, pretreatment as described in methods. NF-κB, pretreatment with ODN. No LPS, mice given sterile saline only at corresponding times). IL-6 levels rapidly rose from the lower limit of detectability (100 pg/ml) at time zero to peak levels (5800 pg/ml) at 4 hrs after ip injection of LPS. Levels remained high (3900 pg/ml) up to 20 hrs after treatment. In contrast, serum levels of IL-6 were almost two fold (51%) lower at 4 hrs after LPS challenge (2900 pg/ml) in mice pretreated with antisense NF-κB ODNs. The serum IL-6 levels at 4 hours in mice pretreated with NAC were not significantly different from the LPS only control (74% or 4300 pg/ml)(FIG. 7).

ANOVA analysis of the 3 groups at 4, 8 and 20 hours, revealed a reduction of IL-6 levels by NAC which was barely significant [p=0.03, F(1,24)=6.68], and a highly significant reduction by NF-κB antisense ODN [p=0.0001, F(1,24)=71.61].

EXAMPLE 5

Tissue Specific Effect of NF-κB Antisense ODNs on LPS Induced IL-6 mRNA

Previous studies in mice have suggested nonuniform accumulation of oligonucleotides in different tissues when administered intraperitoneally or intravenously (Iversen, P. et al., *Anti-cancer Drug Design* 6:531, 1991). Previous studies suggested that oligonucleotide uptake by cells may be highly dependent on activation state (Kitajima, I., et al., *J. Biol. Chem.* 267:25881, 1992). Therefore, the effects of NF-κB antisense on IL-6 in individual tissues in the presence or absense of LPS activation were evaluated. IL-6 mRNA expression was monitored because previous studies have shown that its expression may be pleomorphically induced in a large number of tissues (Ulich, T. R., et al., *J. Immunol* 146:2316, 1991; Troutt, A. B. et al., *J. Cellular Physiology,* 138:38, 1989) and can therefore be used to assess NF-κB inhibition in variety of tissues.

Northern blot analysis. Kidney, liver, lung, spleen and salivary glands from representative mice of each group were rapidly frozen in liquid nitrogen and crushed with a sterile pestle while frozen, mRNA was extracted using the Fast Track method (Bradley, J. E., et al., *BioTechniques* 6:114, 1988)(Invitrogen, San Diego, Calif.). The positive control for murine gene expression (TNF-a, IL-6, MHC class I and GM-CSF), was mRNA obtained from an HTLV-I tax expressing mouse fibrosarcoma cell line (Kitajima, I., et al., *J. Biol. Chem.* 267:25881, 1992). 7 mg mRNA per lane was loaded and electrophoresis was performed on formaldehyde 1.2% agarose gels. Samples were blotted onto nylon membrane and fixed by UV crosslinking. Murine cDNA probes of MHC class I & II and GM-CSF were labeled via the random primer method with [$^{32}$P]dATP. IL-6 TNF-α and actin probes cloned in pUC, pBluescript or pgem plasmids were labeled with [$^{32}$P]dATP by polymerase chain reaction using universal primers complementary to regions flanking the linkers. Specific activities of probes were in excess of $1 \times 10^9$ cpm/mg.

mRNAs were extracted from each tissue, 3 hrs after LPS injection. In FIG. 8, the lanes were as follows: B is an HTLV-I tax transformed cell line which expresses high levels of NF-κB and serves as a positive control. No is obtained from mock (saline treated) mice. LPS, obtained after no pretreatment.

NAC, is from pretreated mice (8 mg×2). NF is from an animal pretreated with 40 mg/g NF-κB antisense ODN. DNA probes (IL-6, TNF-α, MHC class I, GM-CSF and actin) are indicated at the left. Analysis of liver and kidney are shown in panel A and lung, salivary gland and spleen are shown in panel B. Lanes 1-9 represent pretreatment for 3 hours with NAC or antisense NF-κB ODN. Lanes 10-18 show the effects of 24 hrs pretreatment.

Figure 8A:
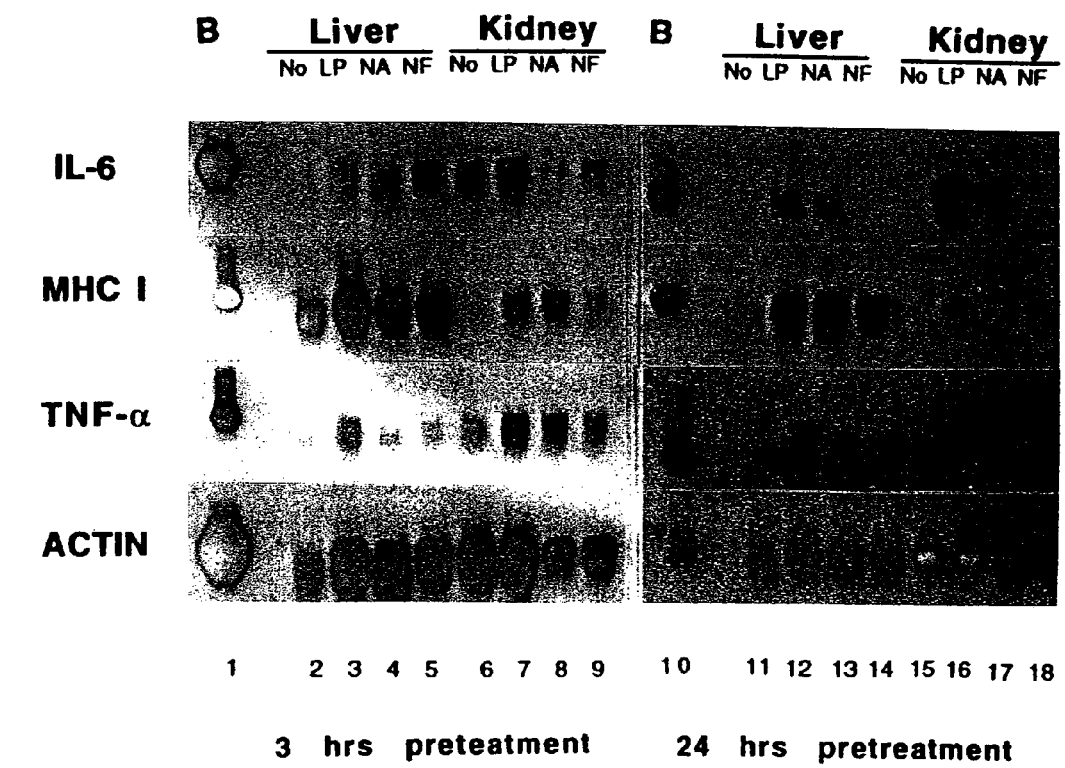
FIGS. 8a and 8b show a Northern blot analysis of NF-κB dependent gene expression in tissues of LPS challenged mice. Lanes 1-9 represent pretreatment for 3 hours with NAC or antisense NF-κB. Lanes 10-18 show the effects of 24 hours pretreatment.
Figure 8B:
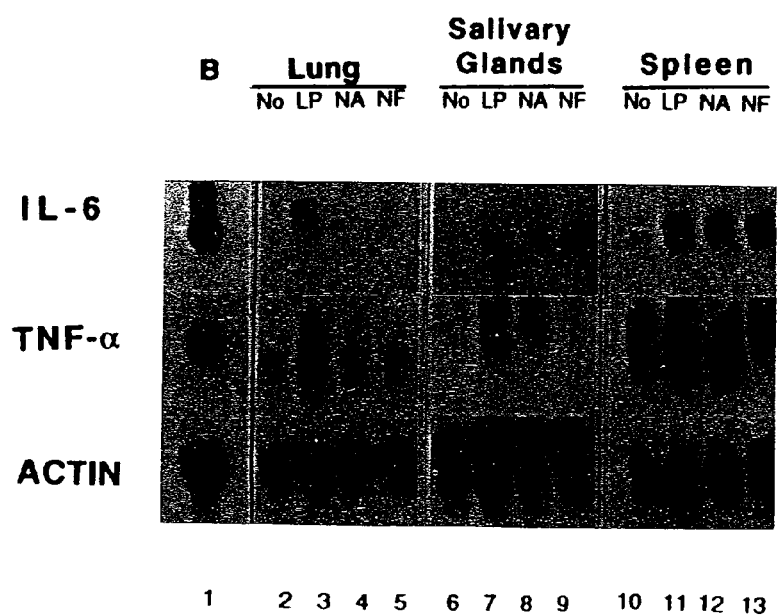

Pretreatment by antisense NF-κB ODNs caused a profound decrease in LPS induced IL-6 mRNA in kidney (FIG. 8A, compare lanes 18 to 16 and 9 to 7), with somewhat less effect in lung (FIG. 8B compare lanes 5 to 3), and lower effect in liver or other tissues. The uptake and inhibitory effect of the oligonucleotides was time dependent as effects were much greater when ODNs were administered 20 hrs rather than 3 hrs prior to LPS (compare right and left hand portions of FIG. 8A). NAC pre-treatment inhibited IL-6 expression in a qualitatively similar manner but was less effective in most tissues tested.

To further confirm the specificity of NF-κB inhibition in tissues, mRNA of two additional genes were analyzed, TNF-α and MHC class I, both known to be NF-κB dependent and implicated in the pathogenesis of sepsis or catastrophic immune responses. Both antisense and NAC down-modulated expression of these genes though the effect was less than that for IL-6 (FIG. 8). FIGS. 8 A and B show that IL-6 mRNA expression was highly induced by LPS in liver, kidney and spleen, moderately induced in lung and weakly induced in salivary gland; IL-6 expression was not detected in brain and muscle.

The invention now being fully described, it will be apparent to one of ordinary skill in the art that various changes and modifications can be made without department from the spirit or scope of the invention.

What is claimed is:

1. A method of treating cancer in a subject comprising administering to a subject a therapeutically effective amount of an oligonucleotide that inhibits NF-κB expression, wherein the oligonucleotide has a sequence comprising at least an 8 nucleotide fragment of SEQ ID NO:6, wherein the oligonucleotide contains not more than 40 nucleotides, thereby treating the cancer.

2. The method of claim 1, wherein the cancer is a solid tumor.

3. The method of claim 1, wherein the cancer is a cancer of B-cells, T-cells or fibroblast cells.

4. The method of claim 3, wherein the T-cell cancer is leukemia.

5. The method of claim 1, wherein the oligonucleotide contains a phosphate backbone that is chemically modified by substitution of a non-bridging oxygen atom of the nucleic acid backbone, wherein said substitution generates a backbone modification comprising a moiety selected from the group consisting of methane phosphate and methyl phosphate.

6. The method of claim 5, wherein the substitution is at one or more nucleotides at the 3' terminus, the 5' terminus, or both terminii of the oligonucleotide.

7. The method of claim 1, wherein the oligonucleotide is DNA.

8. The method of claim 1, wherein the oligonucleotide is RNA.

9. The method of claim 1, wherein the oligonucleotide is SEQ ID NO:6.

10. The method of claim 1, wherein the oligonucleotide is administered in an aqueous or non-aqueous vehicle.

11. The method of claim 1, wherein the oligonucleotide is administered in combination with a glutathione precursor.

\* \* \* \* \*

```
                          SEQUENCE LISTING (1) GENERAL INFORMATION:

(iii) NUMBER OF SEQUENCES: 14

(2) INFORMATION FOR SEQ ID NO: 1:

(i) SEQUENCE CHARACTERISTICS:
         (A) LENGTH: 21 base pairs
         (B) TYPE: nucleic acid
         (C) STRANDEDNESS: single
         (D) TOPOLOGY: linear (ii) MOLECULE TYPE: DNA (genomic)

(vii) IMMEDIATE SOURCE:
         (B) CLONE: p50 S hu (ix) FEATURE:
         (A) NAME/KEY: CDS
         (B) LOCATION: 1..21

(xi) SEQUENCE DESCRIPTION: SEQ ID NO: 1:

ATCTTCACCA TGGCAGACGA T                                                    21

(2) INFORMATION FOR SEQ ID NO: 2:

(i) SEQUENCE CHARACTERISTICS:
         (A) LENGTH: 20 base pairs
         (B) TYPE: nucleic acid
         (C) STRANDEDNESS: single
         (D) TOPOLOGY: linear (ii) MOLECULE TYPE: DNA (genomic)

(vii) IMMEDIATE SOURCE:
         (B) CLONE: p65 S hu (ix) FEATURE:
         (A) NAME/KEY: CDS
         (B) LOCATION: 1..20

(xi) SEQUENCE DESCRIPTION: SEQ ID NO: 2:

CGGCCATGGA CGAACTGTTC                                                      20

(2) INFORMATION FOR SEQ ID NO: 3:
```

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(vii) IMMEDIATE SOURCE:
        (B) CLONE: p50 S mus (ix) FEATURE:
        (A) NAME/KEY: CDS
        (B) LOCATION: 1..20

(xi) SEQUENCE DESCRIPTION: SEQ ID NO: 3:

ATCTTCACCA TGGCAGACGA                                              20

(2) INFORMATION FOR SEQ ID NO: 4:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(vii) IMMEDIATE SOURCE:
        (B) CLONE: p65 S mus (ix) FEATURE:
        (A) NAME/KEY: CDS
        (B) LOCATION: 1..20

(xi) SEQUENCE DESCRIPTION: SEQ ID NO: 4:

TGACCATGGA CGATCTGTTT                                              20

(2) INFORMATION FOR SEQ ID NO: 5:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(vii) IMMEDIATE SOURCE:
        (B) CLONE: p50 AS hu (ix) FEATURE:
        (A) NAME/KEY: CDS
        (B) LOCATION: 1..21

(xi) SEQUENCE DESCRIPTION: SEQ ID NO: 5:

ATCGTCTGCC ATGGTGAAGA T                                            21

(2) INFORMATION FOR SEQ ID NO: 6:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(vii) IMMEDIATE SOURCE:
        (B) CLONE: p65 AS hu (ix) FEATURE:
        (A) NAME/KEY: CDS

```
        (B) LOCATION: 1..20

(xi) SEQUENCE DESCRIPTION: SEQ ID NO: 6:

GAACAGTTCG TCCATGGCCG                                               20

(2) INFORMATION FOR SEQ ID NO: 7:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(vii) IMMEDIATE SOURCE:
        (B) CLONE: p50 AS mus (ix) FEATURE:
        (A) NAME/KEY: CDS
        (B) LOCATION: 1..20

(xi) SEQUENCE DESCRIPTION: SEQ ID NO: 7:

TCGTCTGCCA TGGTGAAGAT                                               20

(2) INFORMATION FOR SEQ ID NO: 8:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(vii) IMMEDIATE SOURCE:
        (B) CLONE: p65 AS mus (ix) FEATURE:
        (A) NAME/KEY: CDS
        (B) LOCATION: 1..20

(xi) SEQUENCE DESCRIPTION: SEQ ID NO: 8:

AAACAGATCG TCCATGGTCA                                               20

(2) INFORMATION FOR SEQ ID NO: 9:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 1..19

(xi) SEQUENCE DESCRIPTION: SEQ ID NO: 9:

GAAGTGGGCC ATGTGGAAG                                                19

(2) INFORMATION FOR SEQ ID NO: 10:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (genomic)
```

(ix) FEATURE:
            (A) NAME/KEY: CDS
            (B) LOCATION: 1..19

(xi) SEQUENCE DESCRIPTION: SEQ ID NO: 10:

CTTCCACATG GCCCACTTC                                                            19

(2) INFORMATION FOR SEQ ID NO: 11:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: DNA (genomic)

(ix) FEATURE:
            (A) NAME/KEY: CDS
            (B) LOCATION: 1..20

(xi) SEQUENCE DESCRIPTION: SEQ ID NO: 11:

AAGCGTGGAG ACAGTTCAGG                                                           20

(2) INFORMATION FOR SEQ ID NO: 12:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: DNA (genomic)

(ix) FEATURE:
            (A) NAME/KEY: CDS
            (B) LOCATION: 1..20

(xi) SEQUENCE DESCRIPTION: SEQ ID NO: 12:

TTGGCGGGGT AAGGACCTTG                                                           20

(2) INFORMATION FOR SEQ ID NO: 13:

(i) SEQUENCE CHARACTERISTICS:
            (A) LENGTH: 35 base pairs
            (B) TYPE: nucleic acid
            (C) STRANDEDNESS: single
            (D) TOPOLOGY: linear (ii) MOLECULE TYPE: DNA (genomic)

(vii) IMMEDIATE SOURCE:
            (B) CLONE: ODN A (ix) FEATURE:
            (A) NAME/KEY: CDS
            (B) LOCATION: 1..35

(xi) SEQUENCE DESCRIPTION: SEQ ID NO: 13:

AGCTTCAACA GAGGGGACTT TCCGAGAGGC TCGAG                                          35

(2) INFORMATION FOR SEQ ID NO: 14:

(i) SEQUENCE CHARACTERISTICS:
            (A) LENGTH: 34 base pairs
            (B) TYPE: nucleic acid
            (C) STRANDEDNESS: single
            (D) TOPOLOGY: linear (ii) MOLECULE TYPE: DNA (genomic)

```
    (vii) IMMEDIATE SOURCE:
          (B) CLONE: ODN c (ix) FEATURE:
         (A) NAME/KEY: CDS
         (B) LOCATION: 1..34

(xi) SEQUENCE DESCRIPTION: SEQ ID NO: 14:

AGCTTCAACG AGGCGACTTT CCGAGAGGCT CGAG                                    34
```